United States Patent [19]

Wiegand et al.

[11] Patent Number: 5,599,914
[45] Date of Patent: Feb. 4, 1997

[54] GLYCOSPHINGOLIPIDS WITH A GROUP CAPABLE OF COUPLING IN THE SPHINGOID PORTION, THE PREPARATION AND USE THEREOF

[75] Inventors: Herbert Wiegand; Silke Bosslet, both of Marburg, Germany

[73] Assignee: Behringwerke Aktiengesellschaft, Marburg, Germany

[21] Appl. No.: 440,798

[22] Filed: Nov. 24, 1989

[30] Foreign Application Priority Data

Nov. 27, 1988 [DE] Germany ............... 38 40 044.8

[51] Int. Cl.$^6$ ............... C07G 3/00; C07G 37/00; C07H 5/04
[52] U.S. Cl. ............... 536/4.1; 536/18.5; 536/18.7; 536/53; 536/55.1; 536/55.3; 530/395
[58] Field of Search ............... 536/53, 4.1, 55.1, 536/18.7, 55.3, 18.5; 514/25; 530/395

[56] References Cited

U.S. PATENT DOCUMENTS

| | | | |
|---|---|---|---|
| 4,757,003 | 7/1988 | Matsumoto et al. | 536/53 |
| 4,849,413 | 7/1989 | Della Valle et al. | 536/53 |
| 4,918,170 | 4/1990 | Hasegawa et al. | 536/1.1 |
| 4,980,462 | 12/1990 | Karlsson et al. | 536/53 |

FOREIGN PATENT DOCUMENTS

| | | | |
|---|---|---|---|
| 0155625 | 9/1985 | European Pat. Off. | 536/53 |
| 3837623.7 | of 1988 | Germany . | |

OTHER PUBLICATIONS

H. Wiegandt and G. Beschang, Z. Naturforschung 206 (1965), pp. 164–166.
H. Wiegandt, Ang. Chem. Intl. Ed. 7 (1968), pp. 87–96.
Pappas et al., Tetrahedron Letters, 36 (1966) pp. 4273–4277.
Wiegandt and Ziegler, Hoppe–Seyler's Physiol. Chem. 355 (1974), pp. 11–18.
Itasaka and Hori, J. Biochem. 85 (1979), pp. 1469–1481.
Carlsson et al, J. Biochem. 173 (1978), pp. 723–737.
Roy et al; J. Carbohydrate Chemistry 6(1):161–165 (1987).
Schwarzmann et al; Biochemistry 22:5041–5048 (1983).
Furst et al; Biol. Chem., Hoppe–Seyler's 369(5):317–328 May 1988.
Laine et al, J. Biol. Chem. 249(14):4460–6 (1974).

*Primary Examiner*—John W. Rollins
*Attorney, Agent, or Firm*—Finnegan, Henderson, Farabow, Garrett & Dunner, L.L.P.

[57] ABSTRACT

The invention relates to the chemical modification of the sphingoid portions of glycosphingolipids. It has been possible by a series of reactions to introduce an amino group in the position of the carbon double-bond in the sphingoid portion after elimination of the long-chain aldehyde. Glycosphingolipids of the formula (2) and (3), where X and Y denote a group capable of coupling, are suitable for coupling to other molecules, preferably proteins. X preferably represents $NH_2$, and Y preferably represents

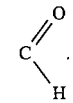

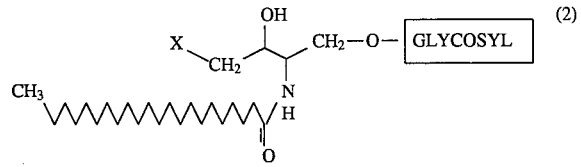

(2)

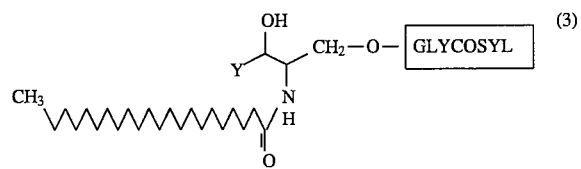

(3)

8 Claims, No Drawings

GLYCOSPHINGOLIPIDS WITH A GROUP CAPABLE OF COUPLING IN THE SPHINGOID PORTION, THE PREPARATION AND USE THEREOF

The invention relates to the chemical modification of the sphingoid portions of glycosphingolipids. It has been possible by a series of reactions to introduce an amino group in the position of the carbon double-bond in the sphingoid portion after elimination of the long-chain aldehyde.

Glycosphingolipids (formula I) are plasma membrane lipids which are composed of a hydrophilic carbohydrate portion and of a hydrophobic ceramide portion. The ceramide portion is composed of sphingosine, a long-chain amino alcohol and a fatty acid bonded as amide.

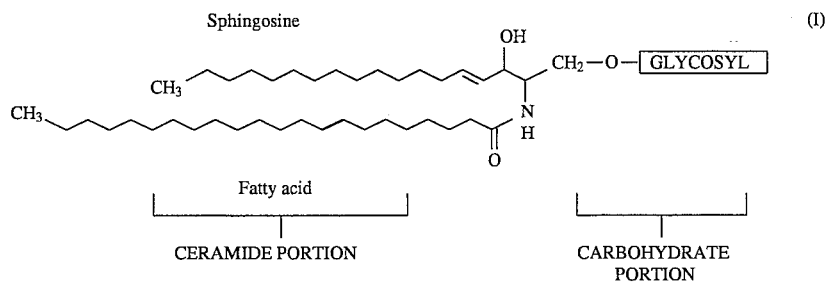

Glycosphingolipids are anchored with this double-tailed hydrophobic portion in the outer plasma membrane in such a way that their oligosaccharide chains project into the extracellular space.

Despite intensive research work, the biological function of glycosphingolipids is not yet accurately known; however, they appear to play a part in the regulation of cell growth and differentiation. Findings which show that, in particular, glycosphingolipids containing sialic acid, gangliosides, occur in a relatively large amount on some tumors of neuroectodermal origin, whereas they are expressed in smaller amounts on normal tissue, have attracted interest to them as tumor-associated antigens for tumor diagnosis and tumor therapy.

The carbohydrate portion is of particular interest in this connection. It has already been shown (German Patent Application P 38 37 623.7) that appropriate sialyl-sugars isolated from a source such as cow colostrum and coupled to a carrier protein are able to imitate epitopes of gangliosides: monoclonal antiganglioside antibodies react with these neoglycoproteins.

In order to be able to establish a more universal targeted coupling which can be applied to all glycosphingolipids, chemical modification of the sphingoid portion of glycosphingolipids is necessary for further work in this area. This relates to the preparation of synthetic glycosphingolipid vaccines. In addition, the introduction of a group capable of coupling is also relevant for problems in basic research, for example glycosphingolipids coupled to reporter enzymes can be employed in histochemical investigations, for example for characterizing mammalian lectins as receptors for glycosphingolipids.

The invention shows that an amino group can, by the reactions described below, be introduced as functional group into the sphingoid portion of glycosphingolipids after elimination of a long-chain aldehyde. During this the glycosidic bonding of the carbohydrate portion to the ceramide portion remains unchanged.

The introduced amino group makes a number of further reactions possible, for example coupling to heterobifunctional reagents for the synthesis of glycosphingolipid conjugates and the use thereof as synthetic vaccines in the therapy of tumors of neuroectodermal origin.

Besides the introduction of an amino group, there is also the possibility of reacting the intermediate (which carries an aldehyde group) directly with other molecules carrying groups capable of coupling, for example amino groups of proteins, coupling reagents etc. It has to be remembered in the reactions that the intermediate with the aldehyde group is not very stable and the carbohydrate portion is eliminated in an alkaline medium.

The principal reactions for introducing the group capable of coupling at the position of the carbon double-bond in the sphingoid portion are as follows:

1. The abovementioned double-bond is cleaved by ozone (H. Wiegandt and G. Baschang, Z. Naturforschung 206, (1965), 164–166) and the methoxy hydroperoxide derivatives which are formed in methanol as intermediates (H. Wiegandt, Ang. Chem. Intl. Ed. 7, (1968) 87–96) are reduced to the aldehyde by addition of dimethyl sulfide (Pappas et al., Tetrahedron Letters, 36 (1966), 4273–4278).

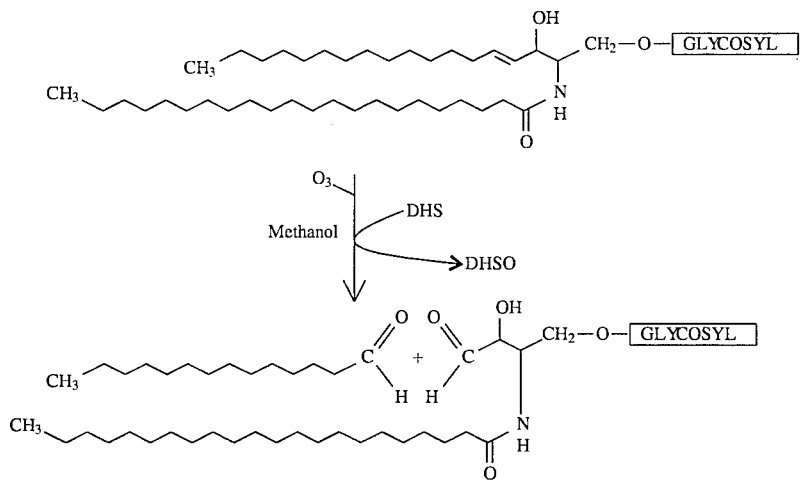

1. The resulting compound is stable only in neutral and acidic media; the carbohydrate portion is eliminated in an alkaline medium.

2. After removal of the long-chain aldehyde by extraction by shaking in hexane, subsequently the ozonolysis product is reductively aminated in methanol with the addition of 1M ammonium acetate and sodium cyanoborohydride (Wiegandt and Ziegler, Hoppe-Seyler's Physiol. Chem. 355, (1974), 11–18).

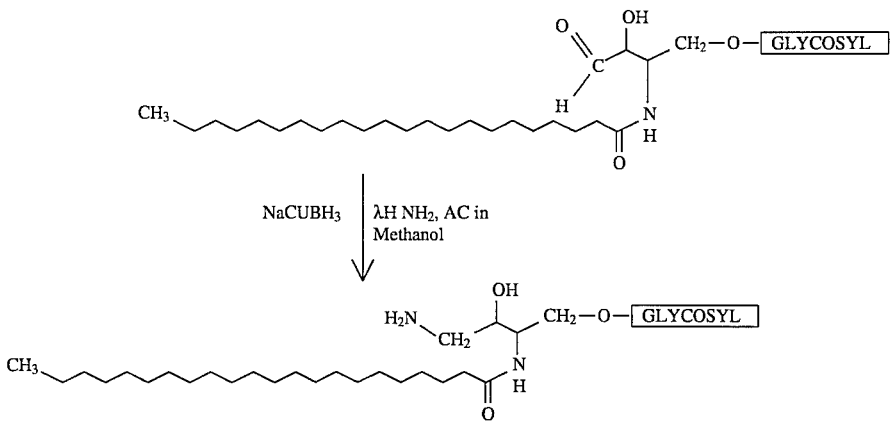

All the reaction steps take place with a very high yield and can be followed by thin-layer chromatography: the mobile phase is chloroform/methanol/water (65:25:4). The reaction products are detected on the thin-layer chromatography plates with iodine vapor or ninhydrin or fluoram and orcinol spray reagent.

The reductively aminated ozonolysis product is ninhydrin- and fluoram-positive on the thin-layer chromatography plate and can be reacted completely with reagents specific for amino groups, such as fluorodinitrobenzene (Sanger's reagent), (Itasaka and Hori, J. Biochem. 85, (1979), 1469–1481) or SPDP (N-succinimidyl 3-(2-pyridyldithio-)propionate) (Carlsson et al., Biochem. J. 173, (1978), 723–737).

Accordingly, the invention relates to glycosphingolipids with a group capable of coupling in the position of the carbon double-bond, there being elimination of a long-chain aldehyde while the molecule remains otherwise intact and, in particular, the glycosidic bonding of the sugar portion is retained, and the group capable of coupling preferably being an amino group or an aldehyde group, and to processes for the preparation thereof and to the use thereof for coupling to suitable reactants and as ingredient of pharmaceuticals.

The invention is furthermore disclosed in the example and the patent claims.

EXAMPLE A

1. Ozonolysis

In a typical reaction mixture, 6 mg of cerebroside (galactosylceramide) were dissolved in 5 ml of methanol and the mixture was ozonolysed (1 bubble/sec) at room temperature until unconsumed ozone was indicated by the violet color of the KJ/starch detection solution.

2. Reduction to the aldehyde

The mixture was subsequently gassed with nitrogen, 30 μl of dimethyl sulfide were added, and the mixture was left to stand overnight. After the solution had been concentrated in a rotary evaporator without heating, the long-chain aldehyde liberated in the ozonolysis was removed by extraction by shaking in hexane (3×2 ml).

3. Reductive amination of the ozonolysis product

The residue from the extraction was dissolved in 4 ml of 1M ammonium acetate in methanol, 15 mg of sodium cyanoborohydride were added, and the mixture was boiled under reflux at 80° C. for 4–5 hours.

The reductively aminated ozonolysis product was subsequently desalted and purified by reversed phase (RP18) chromatography and small silica gel coles.

4. Reaction of the reductively aminated ozonolysis product with fluorodinitrobenzene An aliquot of the reductively aminated ozonolysis product was dissolved in 500 μl of methanol, and 4 drops of triethylamine and 20 μl of 5% fluorodinitrobenzene in ethanol were added to the mixture. The reaction was carried out in 1–2 hours at room temperature, shaking occasionally.

The resulting dinitrophenyl derivative was immediately identifiable because of its yellow color on the thin-layer chromatography plate (HPTLC plate, silica gel 60 (Merck, Darmstadt); mobile phase: chloroform/methanol/water, 65:25:4).

EXAMPLE B

Coupling of reductively aminated ozonolysis products of the gangliosides GM3, GD3, GM2 and GM1 to human serum albumin (HSA) by means of the heterobifunctional coupling reagent N-succinimidyl 3-(2-pyridyldithio)propionate (SPDP); synthesis of conjugates with a derivatization level of 16–18 ganglioside derivatives per HSA molecule 1. Preparation of the reductively aminated ozonolysis products of the gangliosides GM3, GD3, GM2 and GM1

The preparation was carried out as described for cerebroside under 1.–3. in Example A. Mass spectrum analyses of the GM1 and GM3 derivatives confirmed the expected structure.

Subsequent reaction steps:

2. reaction of the reductively aminated ozonolysis products with SPDP 3. reaction of HSA with SPDP 4. reduction of the HSA-SPDP derivative 5. coupling of the ganglioside derivative to the protein derivative and the corresponding detection methods substantially correspond to the method of J. Carlsson et al. (1987) Biochem. J. 173, 723–737 and as proposed in Patent Application DE P 38 37 623.7. Steps 2. and 3. were carried out in 0.1M sodium phosphate buffer, pH 7.5, with a 3- to 5-fold molar excess (based on free epsilon-aminolysyl groups in 3.) of SPDP. The removal of the protein-SPDP derivative from 3. was carried out on a Sephadex G-25 column which was eluted with the buffer for the subsequent reactions (0.1M sodium phosphate buffer, pH 6, 5 mM EDTA). The ganglioside derivatives reacted with SPDP were purified by reversed phase (RP18) chromatography. The individual intermediates were identified by thin-layer chromatography on the basis of the change in the migration behavior on silica gel G-60 plates in the mobile phases chloroform/methanol/ 0.2% aqueous calcium chloride (65:25:4) or (50:40:10).

Step 4. was carried out as follows:

The disulfide bridges newly introduced in the HSA-SPDP derivative by the derivatization were reduced, with the addition of 25 mM dithiothrietol, in 0.1M sodium phosphate buffer, pH 6, 5 mM EDTA, with the elimination of 2-thiopyridone. The native disulfide bridges in the protein are not reduced under these reaction conditions. The reaction was carried out at room temperature, and the reaction time was 1–2 hours.

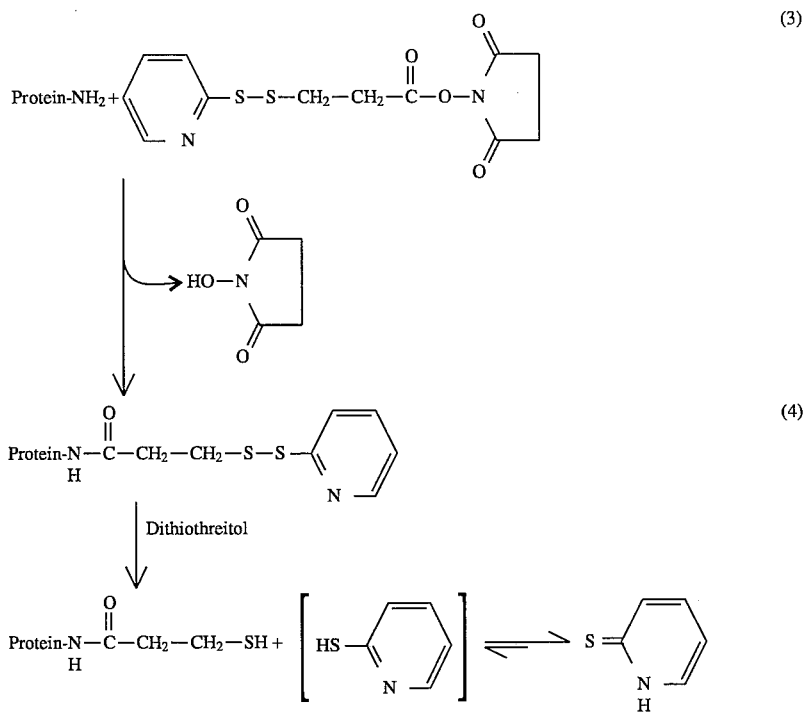

The reduced HSA-SPDP derivative was removed on a Sephadex G-25 column with 0.1M sodium phosphate buffer, pH 6, 5 mM EDTA as eluting buffer.

It was possible by reacting SPDP with excess HSA to prepare specific HSA derivatives with a desired derivatization level.

The ganglioside derivatives were reacted with HSA which was derivatized with 16–18 SPDP molecules. Reaction was complete; the derivatization level of the coupling product was 16–18 ganglioside derivatives (each of the gangliosides GM3, GD3, GM2 and GM1) per HSA molecule.

The specific procedure for the coupling (reaction step 5.) was as follows:

Reduced HSA-SPDP derivative was immediately reacted with the ganglioside-SPDP derivative. The ganglioside-SPDP derivative was employed in a 1–5-fold molar excess based on epsilon-aminolysyl groups in the protein, and the reaction time was 24–48 hours at room temperature.

We claim:

1. A process for the preparation of a compound of the formula (III)

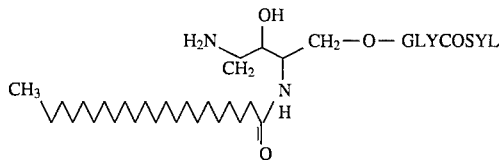

in which glycosyl is the carbohydrate portion of GM3, GD3, GM2 or GM1, which comprises oxidizing a glycosphingolipid of the formula (I)

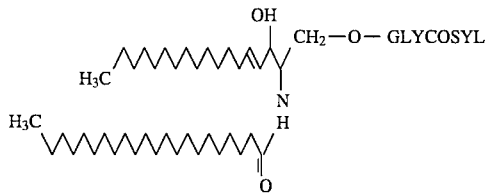

with ozone, and subsequently reducing the reaction product of said oxidizing to a compound of the formula (II),

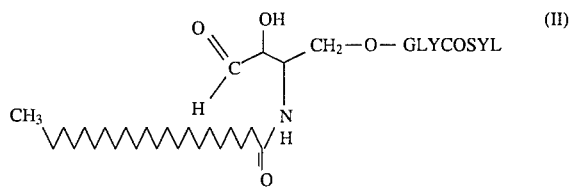

and further comprising the reductive amination of said compound of formula (II) wherein glycosyl is as defined above, with an alkali metal cyanoborohydride.

2. The process as claimed in claim 1 which further comprises coupling a compound of formula (III) through the amino group—$NH_2$ resulting from said reductive amination to another moiety.

3. The method as claimed in claim 2 wherein the other moiety is selected from a heterobifunctional reagent and a protein.

4. The method as claimed in claim 2 wherein the other moiety is a heterobifunctional reagent.

5. The method as claimed in claim 2 wherein the other moiety is a protein.

6. A pharmaceutical which contains a pharmaceutically effective amount of a compound produced by the process of claim 1 coupled to a heterobifunctional reagent.

7. A pharmaceutical which contains a pharmaceutically effective amount of a compound produced by the process of claim 1 coupled to a protein.

8. The process as claimed in claim 1 wherein the reaction product is reduced by addition of dimethyl sulfide.

* * * * *